United States Patent
Bell et al.

(10) Patent No.: US 10,777,311 B2
(45) Date of Patent: *Sep. 15, 2020

(54) SECURE MEDICATION TRANSPORT

(71) Applicant: CareFusion 303, Inc., San Diego, CA (US)

(72) Inventors: Gary Bell, San Diego, CA (US); Gary John Latorraca, San Diego, CA (US); Brendan Burgess, Poway, CA (US)

(73) Assignee: CAREFUSION 303, INC., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/434,631

(22) Filed: Jun. 7, 2019

(65) Prior Publication Data

US 2019/0362832 A1 Nov. 28, 2019

Related U.S. Application Data

(60) Continuation of application No. 15/432,862, filed on Feb. 14, 2017, now Pat. No. 10,318,713, which is a
(Continued)

(51) Int. Cl.
*G16H 20/13* (2018.01)
*G06F 19/00* (2018.01)
(Continued)

(52) U.S. Cl.
CPC ............ *G16H 20/13* (2018.01); *A61J 7/0069* (2013.01); *A61J 7/0084* (2013.01);
(Continued)

(58) Field of Classification Search
CPC . A61J 7/0084; G06F 19/3462; G07F 17/0092
See application file for complete search history.

(56) References Cited

U.S. PATENT DOCUMENTS 6,116,461 A 9/2000 Broadfield et al.
6,294,999 B1 9/2001 Yarin et al.
(Continued)

FOREIGN PATENT DOCUMENTS

CN 1503712 6/2004
CN 101689320 3/2010
(Continued)

OTHER PUBLICATIONS

European Office Action for Application No. 14817711.6, dated Oct. 7, 2019, 9 pages.
(Continued)

*Primary Examiner* — Timothy R Waggoner
(74) *Attorney, Agent, or Firm* — Morgan, Lewis & Bockius LLP

(57) ABSTRACT

A smart carrier has a housing comprising one or more docking locations configured to accept a secure receptacle, a wireless interface module disposed within the housing, and a processor disposed within the housing and operatively coupled to the one or more docking locations and the wireless interface module. The processor is configured to communicate with an external device through the wireless interface module and with a secure receptacle that is mated with one of the one or more docking locations. The smart carrier also has a battery disposed within the housing and configured to provide all operational power to the processor, the wireless interface module, and the one or more docking locations.

20 Claims, 7 Drawing Sheets

Related U.S. Application Data division of application No. 13/931,623, filed on Jun. 28, 2013, now Pat. No. 9,600,634.

(51) Int. Cl.
| | | |
|---|---|---|
| *A61J 7/00* | (2006.01) | |
| *G07F 11/62* | (2006.01) | |
| *G07F 17/00* | (2006.01) | |
| *G07C 9/00* | (2020.01) | |

(52) U.S. Cl.
CPC ..... *G06F 19/3462* (2013.01); *G07C 9/00309* (2013.01); *G07C 9/00912* (2013.01); *G07F 11/62* (2013.01); *G07F 17/0092* (2013.01); *A61J 2200/70* (2013.01); *A61J 2205/60* (2013.01); *G07C 2009/0092* (2013.01); *G07C 2009/00642* (2013.01)

(56) References Cited

U.S. PATENT DOCUMENTS

| | | | |
|---|---|---|---|
| 6,775,591 B1 | 8/2004 | Shoenfeld | |
| 6,955,517 B2 | 10/2005 | Nulman et al. | |
| 7,080,755 B2 | 7/2006 | Handfield et al. | |
| 7,630,789 B2 * | 12/2009 | Broadfield | A61G 12/001 221/98 |
| 7,865,263 B2 | 1/2011 | Spano, Jr. et al. | |
| 7,992,746 B2 | 8/2011 | Weber | |
| 8,234,008 B2 | 7/2012 | Weber | |
| 8,332,066 B2 * | 12/2012 | Weber | G07F 11/62 700/242 |
| 8,335,588 B2 | 12/2012 | Rahilly et al. | |
| 8,417,381 B2 | 4/2013 | Vonk et al. | |
| 8,457,784 B2 | 6/2013 | Rahilly et al. | |
| 8,744,621 B2 | 6/2014 | Michael | |
| 8,983,664 B2 | 3/2015 | Rahilly | |
| 9,355,218 B2 | 5/2016 | Brown et al. | |
| 10,318,713 B2 * | 6/2019 | Bell | G06F 19/3462 |
| 2010/0004780 A1 * | 1/2010 | Rickelhoff | A61G 12/001 700/231 |
| 2012/0004772 A1 | 1/2012 | Rahilly et al. | |
| 2013/0262002 A1 | 10/2013 | Braun et al. | |

FOREIGN PATENT DOCUMENTS

| | | |
|---|---|---|
| CN | 102958490 | 3/2013 |
| EP | 1134641 | 9/2001 |
| WO | WO-0147466 | 7/2001 |
| WO | WO-03048919 | 6/2003 |
| WO | WO-2006002101 | 1/2006 |
| WO | WO-2012163710 | 12/2012 |
| WO | WO-2013006905 | 1/2013 |

OTHER PUBLICATIONS

Australian Examination Report No. 1 for Application No. 2014302614, dated May 11, 2017, 3 pages.
Australian Examination Report No. 2 for Application No. 2014302614, dated Jan. 4, 2018, 4 pages.
Chinese Office Action for Application No. 201480047937.2, dated Jun. 27, 2017, 5 pages excluding translation.
Chinese Office Action for Application No. 201480047937.2, dated Nov. 1, 2016, 8 pages excluding English translation.
Extended European Search Report for Application No. 14817711.6, dated Jun. 9, 2017, 9 pages.
International Search Report and Written Opinion for Application No. PCT/US2014/043949, dated Oct. 15, 2014.
Memo for Mexican Office Action for Application No. MX/a/2015/017930, dated May 20, 2019, 1 page.
India Office Action for Application No. 4206/KOLNP/2015, dated Oct. 23, 2019, 8 pages.
Brazilian Office Action for Application No. BR112015032304-9, dated Dec. 23, 2019, 5 pages.
United Arab Emirates Office Action from KIPO for Application No. UAE/P/1720/2015, first received Dec. 12, 2019, 10 pages.
Canadian Office Action for Application No. 2916610, dated May 29, 2020, 4 pages.

* cited by examiner

SECURE MEDICATION TRANSPORT

CROSS-REFERENCE TO RELATED APPLICATIONS

This application is a continuation patent application of patent application Ser. No. 15/432,862, filed on Feb. 14, 2017, which issued on Jun. 11, 2019, as U.S. Pat. No. 10,318,713 entitled "SECURE MEDICATION TRANSPORT," which is related to and claims priority as a divisional application of, application number Ser. No. 13/931,623, filed on Jun. 28, 2013, which issued on Mar. 21, 2017, as U.S. Pat. No. 9,600,634 entitled "SECURE MEDICATION TRANSPORT," by Gary Bell, et-al. the contents of which are hereby incorporated by reference in their entirety, for all purposes.

BACKGROUND

Field

The present disclosure generally relates to the transport of medications and, in particular, transfer of medications from a pharmacy to a dispensing system.

Description of the Related Art

Patients are routinely prescribed a number of medications while in a hospital. Many hospitals utilize automated dispensing machines (ADMs) to securely store and dispense medications at sites, for example a nursing station, that are remote from the pharmacy. While certain medications are stocked in the ADMs, it is necessary to replenish the stock of medications on a regular basis. In addition, as most ADMs do not have the capacity to store all possible medications, a doctor may prescribe a medication that is not currently stocked in the local ADM and the pharmacy must send this medication to the ADM. Thus, there is a regular transfer of medications from the pharmacy to multiple ADMs within the hospital or, in certain circumstances, to ADMs located in other hospitals.

One method of transferring medications from the pharmacy to an ADM is disclosed in U.S. Pat. No. 6,116,461 to Broadfield et al (hereinafter "the '461 patent"), which is incorporated herein in its entirety. The '461 patent discloses a receptacle with a lid that is held in a closed position, thereby securing the contents of the receptacle, by an internal latch controlled by an internal processor. When the receptacle is docked with a suitable receiving station, such as an ADM, the internal processor is placed in communication with a processor in the receiving station that is further linked to a central data system containing information about medications. The processor of the receiving station may send commands to the internal processor of the receptacle to activate the latch, thereby allowing the lib to be opened. Medications can be transferred from the pharmacy to an ADM by docking a receptacle with a "refill station" in the pharmacy. The '461 patent discloses a process in which the pharmacist or other operator scans a barcode associated with a medication, enters information such as a quantity and expiration date, prints a label that may include medication information in text or barcode form, places the medications in a receptacle and attaches the label to the receptacle, closes the lib, and removes the receptacle from the refill station. The filled receptacle is then placed in a tote and transported to the ADM, the ADM is opened, and the receptacle is docked with the ADM, thereby making the medication available for dispensing from the ADM. One aspect of this system is that the receptacle can be opened only at fixed stations such as a filling station in the pharmacy or the ADM at the nurses' station.

Another conventional method of transferring medications is a manual process wherein medications are placed loose or in plastic bags in totes along with routing sheets. Although most hospitals are taking precautions to separate look-alike/sound-alike medications in compliance with National Patient Safety Goals, there is still opportunity for error as there are thousands of doses of medications available. During the check process, the picked medications are reviewed by scanning the label on the bag and displaying information related to the contents of the bag on a screen for the checker to approve. These medications are collected in totes that are then placed on a mobile cart for transport to the ADM. There is a risk, however, that a tote could be placed directly on the cart and thereby removing medications from the pharmacy without being checked. Furthermore, the medications have the potential to be separated from their routing sheets during handling.

SUMMARY

It is advantageous to provide a mobile carrier that provides power and a communication link to secure receptacles such that the secure receptacles may be filled, checked, and operated at locations other than fixed filling and dispensing systems.

In certain embodiments, a smart carrier is disclosed that has a housing comprising one or more docking locations configured to accept a secure receptacle, a wireless interface module disposed within the housing, and a processor disposed within the housing and operatively coupled to the one or more docking locations and the wireless interface module. The processor is configured to communicate with an external device through the wireless interface module and with a secure receptacle that is mated with one of the one or more docking locations. The smart carrier also has a battery disposed within the housing and configured to provide all operational power to the processor, the wireless interface module, and the one or more docking locations.

In certain embodiments, a system is disclosed that includes a secure receptacle having a body and a lib movable coupled to the body. The lib has a closed position that cooperates with the body to define a compartment. The receptacle also has a lib-securing actuator coupled to the body and configured to engage the lib so as to secure the lib in the closed position when not actuated and to release the lib when actuated. The receptacle also has a processor operatively coupled to the lib-securing actuator. The processor is configured to receive a message and to selectably actuate the lib-securing actuator. The system also includes a smart carrier having a housing comprising one or more docking locations configured to accept the secure receptacle, a wireless interface module disposed within the housing, and a processor disposed within the housing and operatively coupled to the one or more docking locations and the wireless interface module. The processor is configured to communicate with an external device through the wireless interface module and with the processor of a secure receptacle that is mated with one of the one or more docking locations. The smart carrier also has a battery disposed within the housing and configured to provide all operational power to the processor, the wireless interface module, and the one or more docking locations.

In certain embodiments, a method is disclosed that includes the steps of mating a secure receptacle with a portable smart carrier thereby providing power to the secure receptacle from a battery that is disposed within the smart carrier, the battery also providing all operational power to a wireless interface module and a carrier processor that is coupled to the wireless interface module, scanning with a portable user interface device (PUID) a first machine-readable identifier that is associated with a medication, and identifying the mated secure receptacle by scanning with the PUID a second machine-readable identifier disposed on the secure receptacle. The secure receptacle comprises a memory containing a reference identifier and the second machine-readable identifier is associated with the reference identifier in a database. The method also includes the steps of associating the medication with the reference identifier and loading at least one dose of the medication into the secure receptacle.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings.

DETAILED DESCRIPTION

Figure 1:
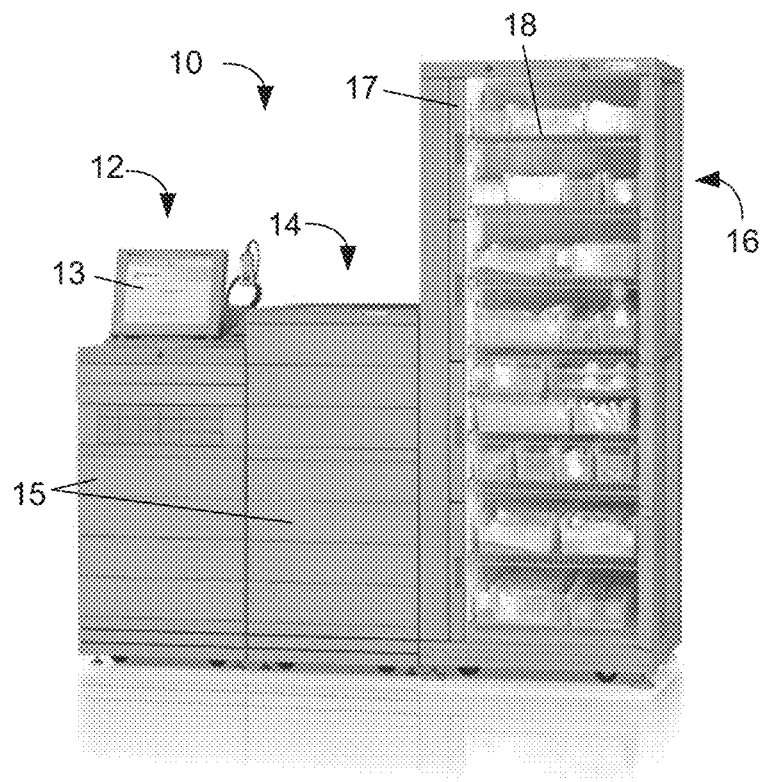
FIG. 1. depicts an example dispensing system.

It is advantageous to provide a mobile carrier that provides power and a communication link to secure receptacles such that the secure receptacles may be filled, checked, and operated at locations other than fixed filling and dispensing systems.

The disclosed systems and methods of secure medication transport automate the pick-check-delivery process to provide increased security during medication replenishment throughout a hospital as well as remote site locations.

In the following detailed description, numerous specific details are set forth to provide a full understanding of the present disclosure. It will be apparent, however, to one ordinarily skilled in the art that embodiments of the present disclosure may be practiced without some of the specific details. In other instances, well-known structures and techniques have not been shown in detail so as not to obscure the disclosure. In the referenced drawings, like numbered elements are the same or essentially similar. Reference numbers may have letter suffixes appended to indicate separate instances of a common element while being referred to generically by the same number without a suffix letter.

While the discussion herein is directed to the management of medications in a hospital, the disclosed concepts and methods may be applied to other fields that would also benefit from a secure method of distribution and dispensing. For example, valuable tools may be managed with this system in a service facility.

Within this document, the term "battery" means energy storage devices conventionally referred to as batteries, for example non-rechargeable carbon batteries and rechargeable nickel-cadmium batteries, as well as all other types of portable power source, including but not limited to energy storage devices, such as a capacitor, energy conversion devices, such as a photovoltaic cell, and energy generation devices, such as a fuel cell, or combinations thereof.

Within this document, the phrases "portable user interface device" and "PUID" mean any mobile device that provides information and accepts input. A PUID may provide information via any channel including but not limited to an optical display such as a light-emitting diode (LED) screen and an audible actuator such as a speaker or buzzer. A PUID may accept input via any channel including but not limited to an optical scanner, a radio-frequency identification (RFID) reader including electric-field and magnetic-field systems, a keyboard, a touchscreen or stylus-activated screen, a microphone, and a joystick. PUIDs may include but are not limited to tablet computers, laptop computers, desktop computers installed on a mobile platform, personal data assistants (PDAs), cellular phones, wirelessly connected devices such as iPods and iPads, and readers such as Kindle e-readers.

Within this document, the term "medication" comprises substances that are conventionally considered to be medications, particularly substances that are available only by a doctor's prescription, as well as any other substance or mixture that may be used in a health-related treatment of a patient. Medications include but are not limited to medical fluids such as a saline solution or Ringer's lactate, active compounds such as an analgesic and an antimicrobial, and health-related substances such as a vitamin.

Within this document, the term "scanning" means the input of a machine-readable feature and interpretation of the information encoded therein. Scanning may include passive optical observation and recording of a visual image, such as a barcode or 2D coded matrix, or may include active illumination, such as provision of a light beam that traverses a portion of the image, as is commonly done in a barcode scanner. Scanning may also include provision of an energizing field, such as an electric field or magnetic field as are commonly provided to read passive RFID tags.

Within this document, the term "portable" means a size and weight that is easily moved by an adult. While an object of any size and weight can be moved, with the use of appropriate equipment, a portable device as considered herein would include devices of a size and weight that they would not be burdensome to a person to keep with them for several hours over the course of an 8-hour workday. Portable devices may be mounted on a rolling cart or other movable appliance, such as the wheeled computer platforms commonly used in hospitals and known to those of skill in the art. Portable devices are not secured to a single location for extended periods of time during which the devices are used.

FIG. 1. depicts an example dispensing system 10. This system 10 includes an ADM 12 with a plurality of drawers 15 connected to an auxiliary cabinet 14 having a plurality of drawers 15 and a tall auxiliary cabinet 16 with a plurality of doors 17 and shelves 18. In one mode of operation, the drawers 15 and doors 17 are secured such that the contents are not available for removal. The ADM 12 includes a user interface 13 and a processor (not visible in FIG. 1) that accepts input from the user through the user interface 13. An example dispensing process would begin with a user identifying themselves to the ADM 12, for example by providing a login name and password through the user interface 13. The ADM processor verifies that the identified user is authorized to remove at least one item from the ADM 12, or attached auxiliary cabinets 14 and 16, and activates an item-selection display. The user selects an item to be dispensed. The ADM processor verifies that the user is authorized to remove the selected item and unlocks the drawer 15 or door 17 that contains the selected item. The user removes the item, closes the drawer 15 or door 17, and logs out, whereupon the ADM 12 locks the opened drawer 15 or door 17.

Figure 2:
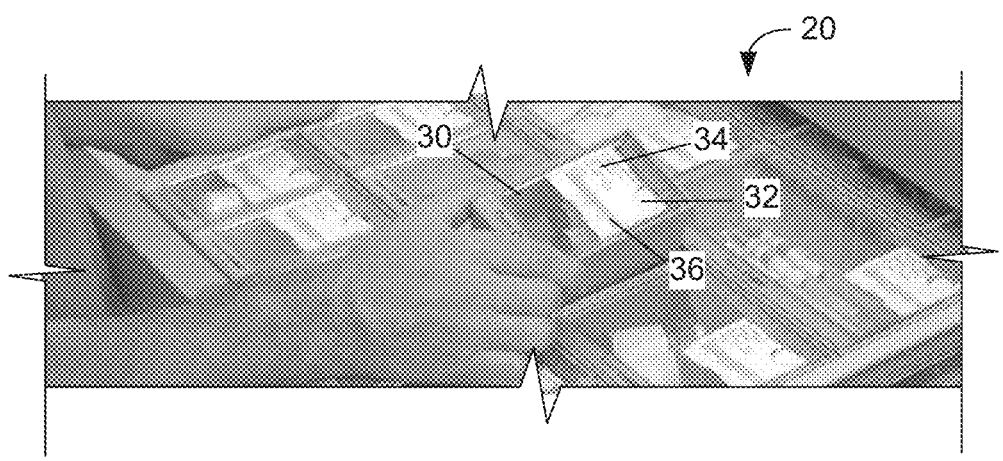
FIG. 2 depicts an open drawer of the ADM of FIG. 1 and the conventional receptacles contained therein.

FIG. 2 depicts an open drawer 20 of the ADM 12 of FIG. 1 and the conventional receptacles 30 contained therein. The receptacles 30 are as disclosed in the '461 patent and are marked with a label 32 that is printed at the time of filling of the receptacle 30. The label 32 includes text 34 that provides information regarding the medication contained in the receptacle 30, for example the medication name, dose, and expiration date. The label 32 also includes a barcode 36 that may contain a portion of the same information or additional information, such as a tracking number associated with the latest filling of this particular receptacle 30. The receptacle 30 may also include a non-volatile memory (not visible in FIG. 2) that stores a unique identification number associated with this receptacle 30. When the receptacle 30 is plugged into the drawer 20, the ADM processor of the ADM 12 can communicate with the memory of the receptacle 30 and retrieve the identification number associated with this receptacle 30. In some systems, a central database (not shown in FIG. 2) contains a list of identification numbers and information regarding the contents of the respective receptacles 30 and the ADM 12 can communicate with this database to retrieve this information. Thus, plugging a receptacle 30 into the drawer 20 informs the processor of the ADM 12 of the contents of that receptacle 30.

Figure 3:
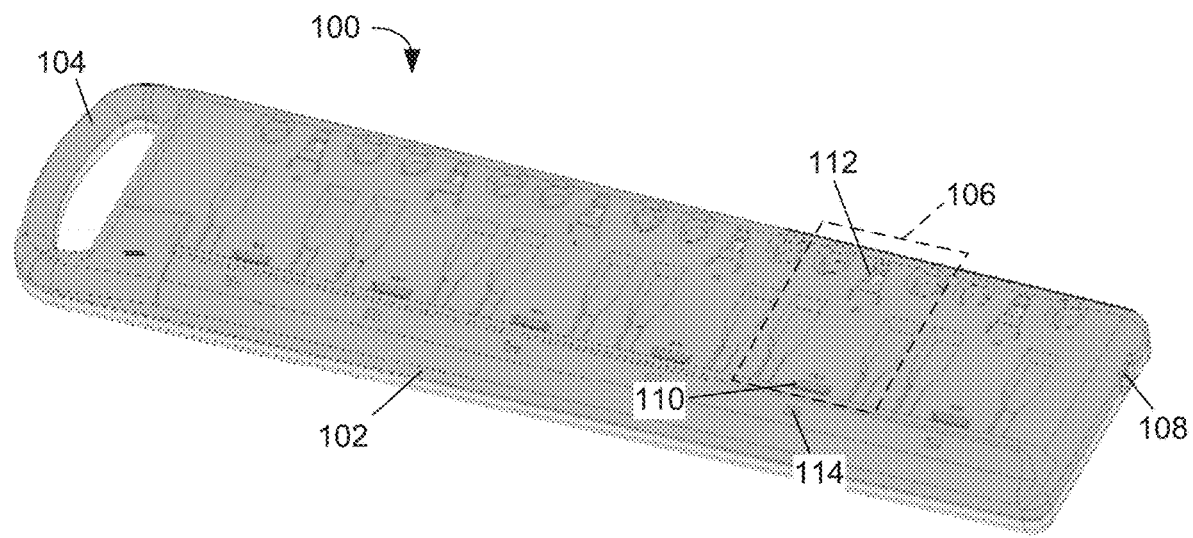
FIG. 3 depicts an exemplary smart carrier according to certain aspects of the present disclosure.

FIG. 3 depicts an exemplary portable smart carrier 100 according to certain aspects of the present disclosure. This embodiment of the smart carrier 100 comprises a body 102 with a handle 104, a plurality of docking locations 106, a processor 120 (not visible in FIG. 3, shown in FIG. 5), and an external connector 108. In general, the smart carrier 100 is sized to be portable and easily carried, for example by the handle 104, and transported, for example on a cart. Each of the docking locations 106 comprises a connector 110, a retention feature 112, and an indicator 114. In certain embodiments, the connector 110 includes electrical contacts (not visible in FIG. 3) that may provide one or more of power, ground, and communication lines. In certain embodiments, the retention feature 112 comprises a detent element (not visible in FIG. 3) that retains a latching feature of a secure receptacle (not shown in FIG. 3) until the applied removal force exceeds a predetermined value. In certain embodiments, the retention feature 112 comprises a locking element (not visible in FIG. 3) that retains a latching feature of a secure receptacle (not shown in FIG. 3) until the locking element is unlocked by a command from the processor 120. In certain embodiments, the indicator 114 comprises a visual indicator, for example a light-emitting diode (LED). Additional features and capabilities of the smart carrier 100 are discussed with respect to FIG. 5.

Figure 4A:
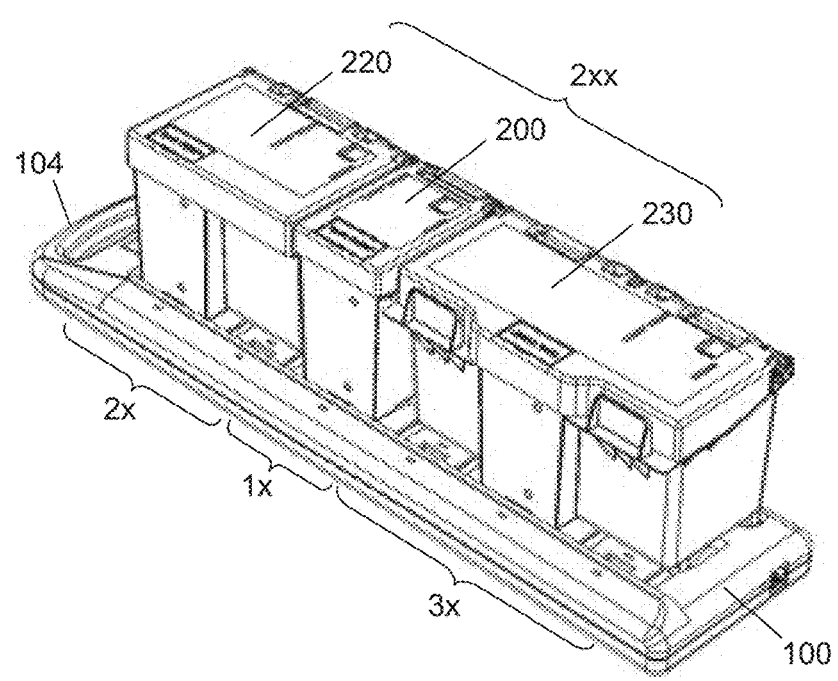
FIG. 4A depicts a plurality of exemplary secure receptacles attached to a smart carrier according to certain aspects of the present disclosure.

FIG. 4A depicts a plurality of exemplary secure receptacles 2xx, referring generically to all configurations of secure receptacles that may come in various sizes, attached to a smart carrier 100 according to certain aspects of the present disclosure. The example smart carrier 100 of FIG. 3 has six docking locations 106, each configured to accept a "one wide" or "1×" secure receptacle 200, as shown in FIG. 4A wherein a 1× secure receptacle 200 is docked in the third docking location 106 from the handle 104.

Larger secure receptacles 2xx may occupy two or more adjacent docking locations 106. For example, a "two-wide" or "2×" secure receptacle 220 is shown docked in the first and second docking locations 106. Similarly, a "three-wide" or "3×" secure receptacle 230 is shown docked to the fourth, fifth, and sixth docking locations 106. In this example, the secure receptacle 230 is in operative contact only with the contact 110 of the fifth docking location 106, as the contacts 110 of the fourth and sixth docking locations 106 are exposed with the secure receptacle 230 in place. In certain embodiments, the secure receptacle 230 may engage only the retention feature 112 of the fifth docking location 106, while in other embodiments the secure receptacle 230 may engage one or both of the retention features 112 of the fourth and sixth docking locations 106.

Figure 4B:
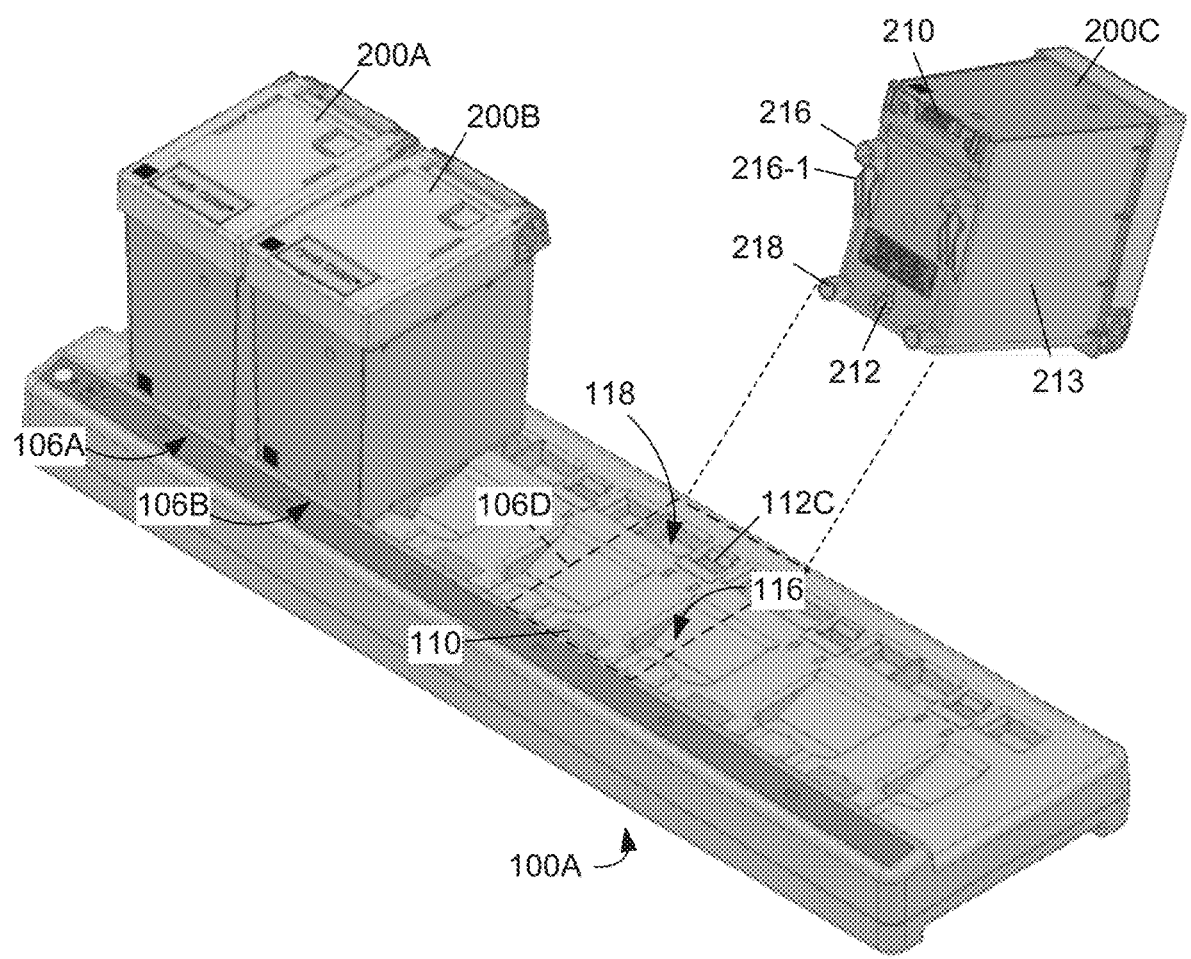
FIG. 4B depicts the corresponding features of another embodiment of a secure receptacle and another embodiment of a smart carrier according to certain aspects of the present disclosure.

FIG. 4B depicts the corresponding features of another embodiment of a secure receptacle 200 and another embodiment 100A of a smart carrier according to certain aspects of the present disclosure. Two 1× secure receptacles 200A and 200B are shown as docked in the first and second docking locations that are identical and are designated 106A and 106B for convenient specific identification. A third 1× secure receptacle 200C is shown in an orientation that exposes the features that mate with elements of a docking location 106, and the specific docking location 106D is used herein as an example of such. The secure receptacle 200C has a body 213 with a pair of front feet 216 that include a shaped surface 216-1 and a pair of rear feet 218. The rear feet 218 fit into the pockets 118 and the front feet 216 fit into the recesses 116 when the secure receptacle 200C is mated with docking location 106D. In this embodiment, the recesses 116 are formed such that one of the front feet 216 of adjacent secure receptacles 2xx fit into a common recess 116 while the pockets 118 are configured to accept individual rear feet 218. In other embodiments, the pockets 118 and recesses 116 may be provided in other configurations to accept single or multiple feet from one or multiple secure receptacles.

There is an interface connector 210 that will mate with docking connector 110 when the secure receptacle 200C is docked with docking location 106D. There is also a latching feature 212 on the body 213 that engages a retention feature 112 of the smart carrier 100A. In certain embodiments, the interface connector 210 and docking connector 110 may be replaced with a wireless communication link, for example inductively coupled plates, that allow communication and power to be transferred between the smart carrier 100 and secure receptacle 200 without direct electrical contact.

Figure 4C:
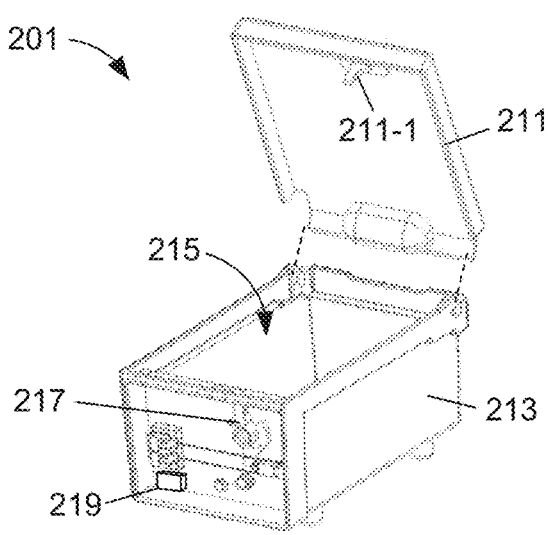
FIG. 4C is a partially exploded view of another secure receptacle 201 according to certain aspects of the present disclosure.

FIG. 4C is a partially exploded view of another secure receptacle 201 according to certain aspects of the present disclosure. Secure receptacle 201 is a "half-height" version of the 1× "full height" secure receptacle 200 shown in FIGS. 4A and 4B, wherein the width and depth of the secure receptacles 200 and 201 are the same, and the features shown in FIG. 4B are common and identical for both, while the height of the secure receptacle 201 is less than the height of the secure receptacle 200. The lib 211 is movably coupled to the body 213 and, in certain embodiments, the lib 211 is hingedly attached to the body 213 at a back edge of the body 213. In certain embodiments, the lib 211 is the same on a half-height secure receptacle 201 and a full-height secure receptacle 200 of the same width and depth.

A front cover has been removed from the body 213 to expose certain internal elements, including a processor 219 and a lib-securing actuator 217 that is configured to engage a latching feature such as the hook 211-1 of the lib 211. In certain embodiments, the lib-securing actuator 217 is configured to engage and retain the hook 211-1 so as to secure the lib 211 in a closed position, for example as shown by secure receptacle 200A in FIG. 4B. The processor 219 is operatively coupled to the lib-retaining actuator 217 and the interface connector 110 (not visible in FIG. 4C). When the lib 211 is closed, the lib 211 cooperates with the body 213 to define a compartment 215. After the lib is closed, any items placed in the compartment 215 are secure until the secure receptacle 200 is docked with a receiving station such as a smart carrier 100 and a command is received by the processor 219 through the interface connector 210 to open the lib, whereupon the processor actuates the lib-retaining actuator 217 which releases the hook 211-1 and allows the lib 211 to open. In certain embodiments, the secure receptacle 201 may comprise a biasing element, such as a spring, that urges the lib 211 to move away from the closed position to an open position such that the lib 211 will self-open upon release of the hook 211-1 by the lib-securing actuator 217.

Figure 5:
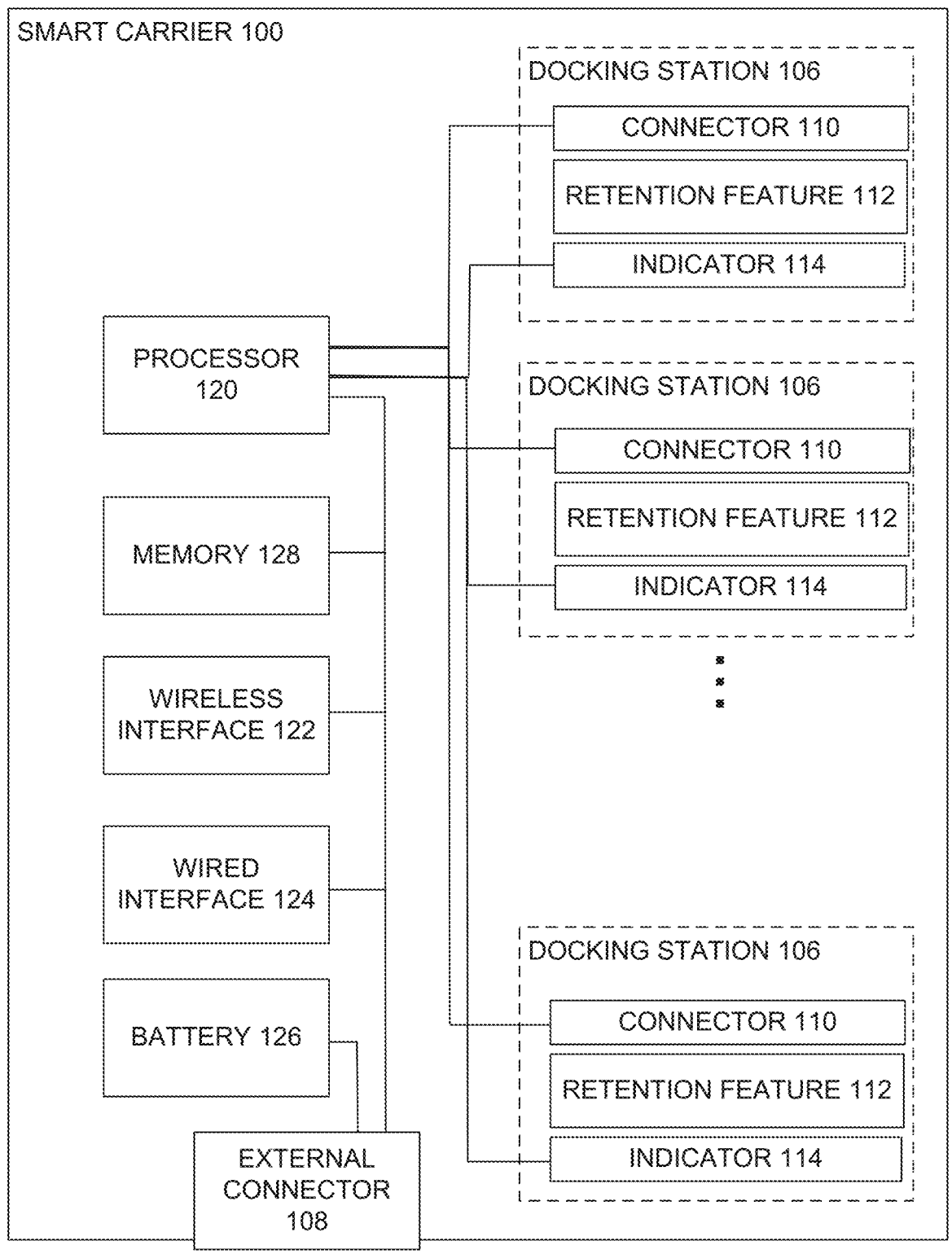
FIG. 5 is a block diagram of an exemplary smart carrier according to certain aspects of the present disclosure.

FIG. 5 is a block diagram of an exemplary smart carrier 100 according to certain aspects of the present disclosure. There may be one or more docking locations 106 in a smart carrier 100, wherein each docking location 106 may have a connector 110, a retention feature 112, and an indicator 114. A processor 120 is operatively coupled to the connectors 110 and the indicators 114. The processor 120 is also coupled to a memory 128, a wireless interface module 122, a wired interface module 124, and an external connector 108.

In certain embodiments, the wireless interface 122 is configured to bidirectionally communicate with a wireless network (shown in FIG. 6), for example an 802.11 network, and communicate with an external device (shown in FIG. 6) through the network. In certain embodiments, the wired interface module 124 is configured to communicate with a wired network, for example an Ethernet network, through the external connector 108 and communicate with an external device through the network. The smart carrier 100 also comprises a battery 126, or other portable power source, that may be operatively coupled to the external connector 108, for example to accept recharging current, and provides all operational power to the elements of the smart carrier 100. In certain embodiments, the battery 126 may not be coupled to the external connector 108 and must be periodically replaced. The battery 126 is operatively coupled to at least one of the processor 120, wireless interface module 122, wired interface module 123, connectors 110, and indicators 114, although these connections have been omitted in FIG. 5 for clarity as the distribution of power in an electronics system will be known to those of skill in the art.

In certain embodiments, the memory 128 is configured to store a carrier identifier that is associated with the individual smart carrier 100. When a secure receptacle 2×× is docked with one of the docking locations 106, the processor 120 may communicate with the processor 219 of the secure receptacle 2×× and retrieve a reference identifier that is associated with the individual secure receptacle 2××. The processor 120 may then send the reference identifier of the secure receptacle 200 and the carrier identifier to a server, though either the wired interface module 124 or the wireless interface module 122, such that the server knows that this particular secure receptacle 2×× is operatively docked with this particular smart carrier 100.

The processor 120 may also be configured to monitor the condition of the battery 126, for example one or more of the current state of charge, the provided voltage, the elapsed time since replacement, and the number of recharge cycles, and report one or more of these parameters to an external device.

Upon receipt of certain commands, for example a command to move a docked secure receptacle 200 from the smart carrier 100 to an ADM 12, the processor may activate an indicator 114 associated with one of the docking locations 106.

Figure 6:
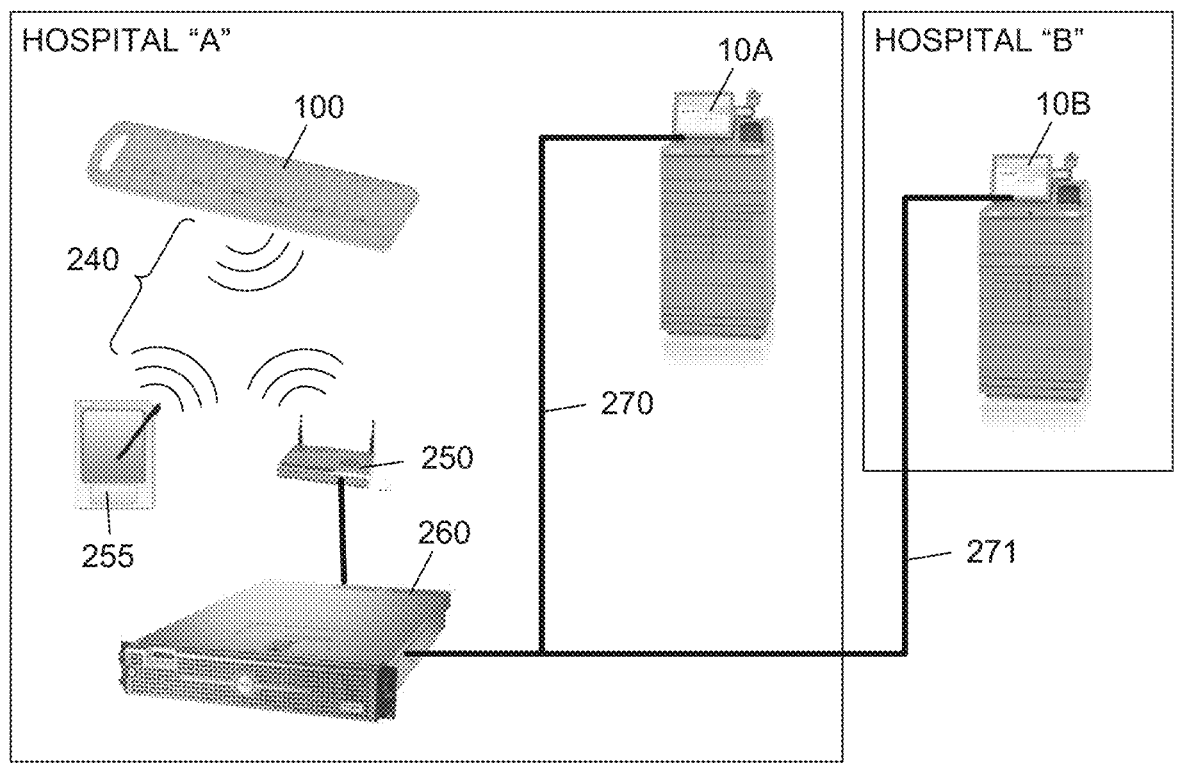
FIG. 6 is a schematic representation of an exemplary network according to certain aspects of the present disclosure.

FIG. 6 is a schematic representation of an exemplary network 240,270 according to certain aspects of the present disclosure. There is a server 260 located in a "hospital A" that is attached to a wired network 270 and a wireless network 240 through an access point 250. A dispensing system 10A in the same building as the server 260 is also connected to the wired network 270 and in communication with the server 260. The server 260 includes a memory (not visible in FIG. 6) that is configured to store operating instructions and one or more databases. At least one of the databases includes a listing of the reference identifiers that are associated with secure receptacles 200 that are in use within the hospital A. This database or other databases may include a list of patients and their locations, which may be part of or related to an "admit-discharge-move" or "ADM" system, and a list of prescribed medications.

Once a secure receptacle 200 is filled with a certain number of doses of a medication, the database of the server 260 may store information about the contents of the secure receptacle 200 in association with the reference identifier, which is the sole element of information stored in the processor 219 of the secure receptacle 200, thereby treating the reference identifier similar to a "license plate" wherein the reference identifier does not contain any information about the contents of the secure receptacle 200 but can be used to access this information in the database of the server 260. In other embodiments, a copy of a portion of the information that is stored in the database of the server 260 may be copied into a memory of the processor 219 of the secure receptacle 200 such that a recipient device, for example a dispensing system 10, may retrieve the information about the contents of the secure receptacle 200 from the processor 219 without a need to communicate with the sever 260.

Figures 8, 9:
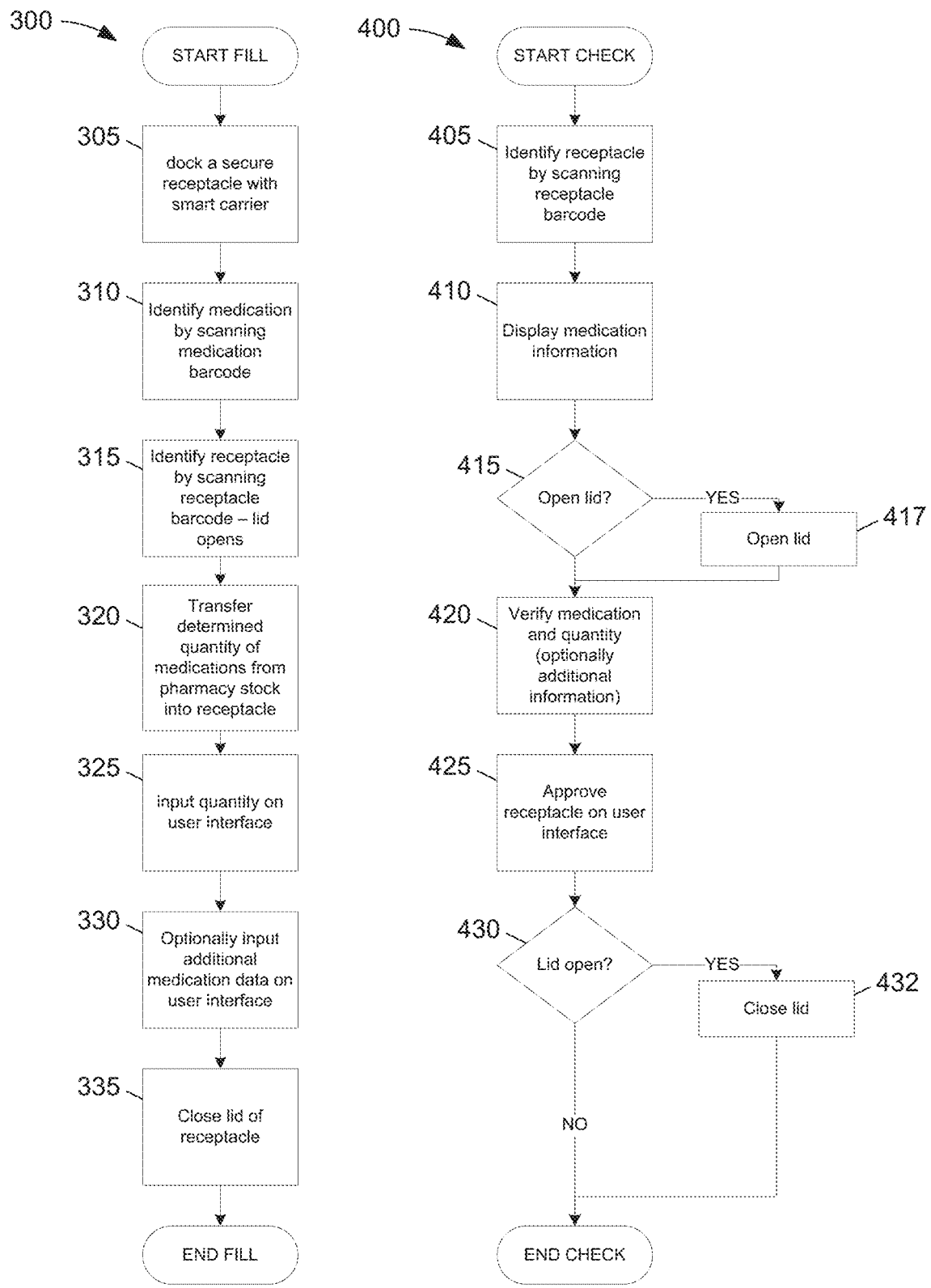
FIG. 8 is a flow chart of an exemplary fill process according to certain aspects of the present disclosure.
FIG. 9 is a flow chart of an exemplary check process according to certain aspects of the present disclosure.
Figure 10:
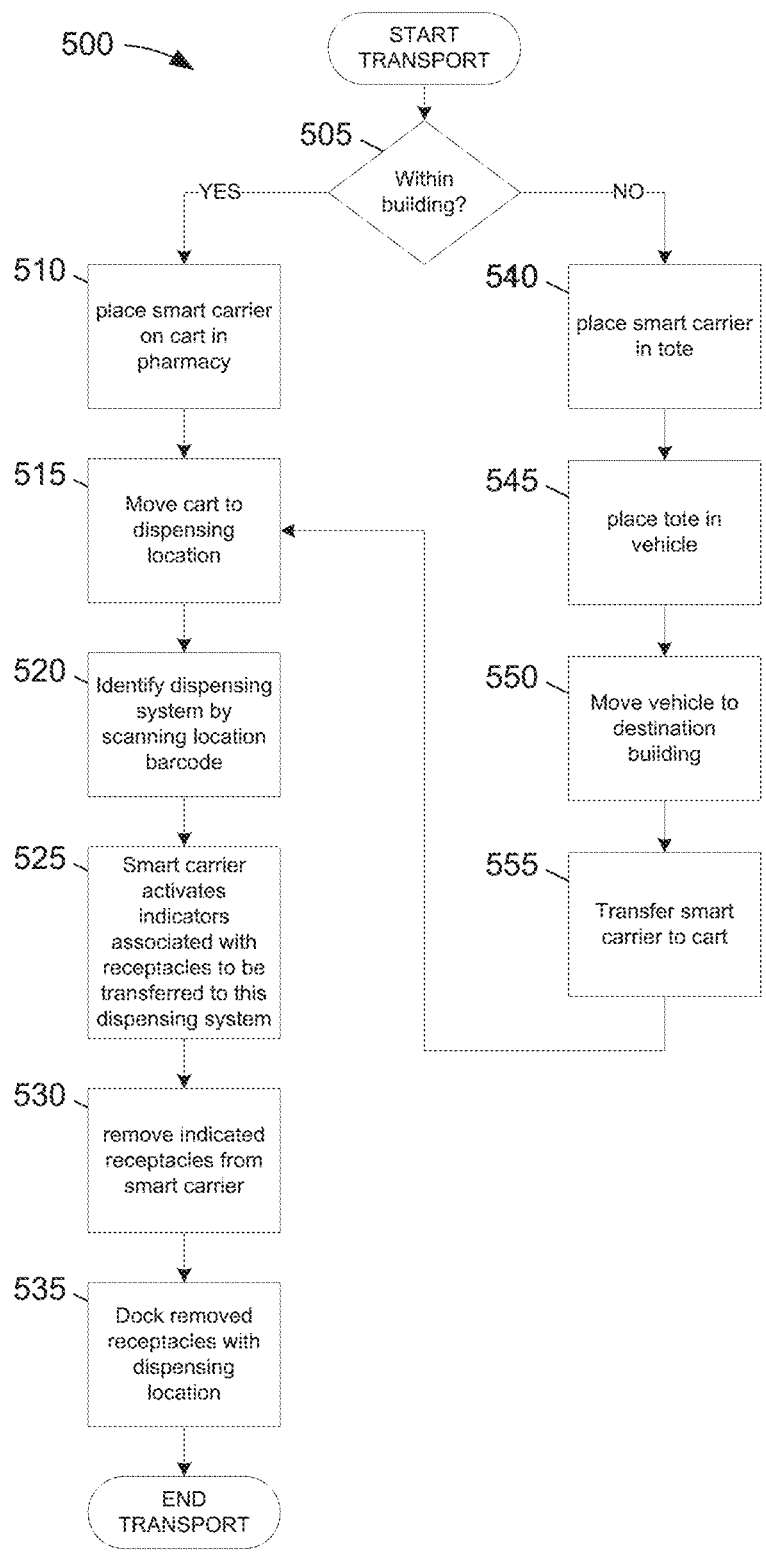
FIG. 10 is a flow chart of an exemplary transport process according to certain aspects of the present disclosure.

FIG. 6 also shows a portable user interface device (PUID) 255 that may be used in conjunction with the smart carrier 100. Example processes are shown in FIGS. 8-10. The PUID 255, shown in FIG. 6 as a stylus-activated tablet, may be wirelessly connected through the wireless network 240 and access point 250 to the server 260 and can provide input from the user as well as receive and display information sent from by the server 260 to the PUID 255. The PUID 255 may include the ability to scan and interpret machine-readable identifiers, for example a barcode or 2D code, as may be used to identify a medication or a device. In certain embodiments, the PUID 255 does not interact directly with a smart carrier 100. In other embodiments, a PUID 255 be provided with a reference identifier of a smart carrier 100, for example by scanning a carrier identifier that is available as a barcode attached to the smart carrier 100 and sending this scanned carrier identifier to the server 260, which responds with the reference identifier associated with the scanned carrier identifier and thereby enables the PUID 255 to interact directly with the smart carrier 100. In other embodiments, a PUID 255 may be linked to a local smart carrier 100 through a process similar to pairing of Bluetooth® devices as is known to those of skill in the art.

The server 260 may also be connected to dispensing system 10B located in another building, for example a hospital "B." The wired network 271 that connects to the other building may include a dedicated line, such as a T1 line, between hospitals A and B or an intermittent connection, for example through the internet.

For an example of an order to deliver a medication to a specific dispensing system 10, the server 260 can exchange information with the PUID 255 as part of the filling process 300, discussed in greater detail with respect to FIG. 8, and then provide the destination dispensing system 10 with information related to the secure receptacle 200 that contains the medication to be delivered to that dispensing system 10.

Figure 7:
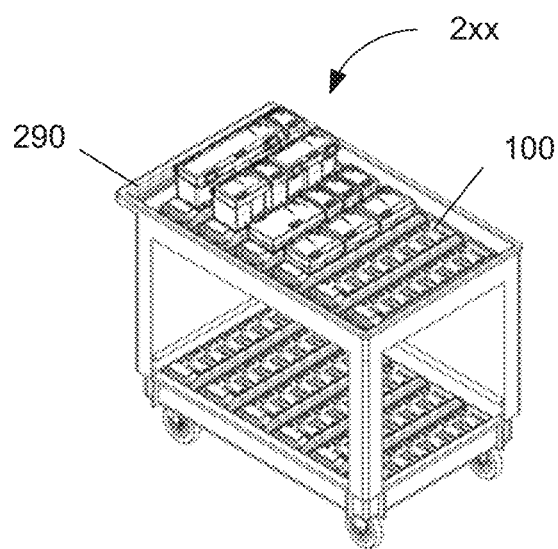
FIG. 7 depicts an exemplary cart with a plurality of smart carriers and secure receptacles according to certain aspects of the present disclosure.

FIG. 7 depicts an exemplary cart 290 with a plurality of smart carriers 100 and secure receptacles 200 according to certain aspects of the present disclosure. As the smart carriers 100 are portable and self-contained, i.e. can function while separated from any source of power, a cart 290 is a convenient way to carry and use multiple smart carriers 100. In certain embodiments, the cart 290 may be configured to pass through stock shelves within a pharmacy so as to enable a pharmacy technician to fill secure receptacles 200 at the storage location of a medication, rather than having to carry multiple doses of the medication to a fixed filling station within the pharmacy. In certain embodiments, the cart may be configured to transfer the secure receptacles 2×× from the pharmacy to one or more dispensing systems, for example the dispensing system 10 of FIG. 1. In certain embodiments, the cart 290 may comprise storage features such as drawers, storages compartments with doors, or other storage arrangements as will be known to those of skill in the art. In certain embodiments, one or more of these storage features may be lockable as will be known to those of skill in the art, thereby providing secure storage during transport.

FIG. 8 is a flow chart of an exemplary fill process 300 according to certain aspects of the present disclosure. The process will be described with reference to the smart carrier 100 and secure receptacle 200 for convenience, although it will apparent to those of skill in the art how similar processes may be accomplished with alternate embodiments of either device. The process starts at step 305 when a user, for example a pharmacy technician, docks a secure receptacle 200 with one of the docking locations 106 of a secure carrier 100. The processor 120 of the smart carrier 100 establishes communication with the processor 219 of the secure receptacle 200 and retrieves a reference identifier from the processor 219. The processor 120 sends this reference identifier to a server 260. The user then uses a PUID 255 in step 310 to scan a machine-readable medication identifier, for example a barcode, that is associated with a medication, for example printed on a container of the medication. The user then uses the PUID 255 in step 315 to scan a machine-readable receptacle identifier, for example a barcode, that is associated with the docked secure receptacle 200, for example printed on the lib 112 of the secure receptacle 200. The PUID 255 provides the medication and receptacle identifiers to the server 260, which compares the receptacle identifier to a list of associated reference identifiers and receptacle identifiers, for example a list contained in a database stored in a memory attached to the server 260. The server 260 determines the reference identifier that is associated with the provided receptacle identifier and creates a fill record in the database that the identified secure receptacle 200 that is associated with the provided receptacle identifier is being filled with the medication associated with the provided medication identifier.

As part of step 315, the server 260 sends a "lib open" command to the processor 120 to open the lib 112 of the docked secure receptacle 200. The processor 120 sends a command to the processor 219 to open the lib 112, and the processor 219 actuates the lib-securing actuator 217, thereby releasing the lib 112 that, in this example, self-opens under the urging of a spring. The user proceeds to step 320 and transfers a determined quantity of the medication into the compartment 215 of the secure receptacle 200, inputs the quantity transferred into the PUID 255 in step 325 and optionally enters additional information, for example an expiration date, in step 330. The PUID 255 sends this information to the server 260, which updates the previously created fill record. The user then closes the lib 112 in step 335, whereupon the processor 219 sends a signal to the processor 120 that the lib 112 is closed. The processor 120 forwards this information to the server 260, which closes the fill record as complete, thereby completing the fill process 300.

FIG. 9 is a flow chart of an exemplary check process 400 according to certain aspects of the present disclosure. For this example, it is presumed that the check process 400 follows the fill process 300 and that the secure receptacle 200 is still attached to the smart carrier 100. The process starts at step 405 when a user, for example a licensed pharmacist, uses the PUID 255 to scan the machine-readable receptacle identifier on the docked secure receptacle 200. The PUID 255 sends the receptacle identifier to the server 260, which retrieves the fill record and sends this information to the PUID 255, which displays this information in step 410. If the user wishes to open the lib 112 to directly inspect the medications in the compartment 215, the user may optionally input a command into the PUID in step 415 to open the lib 112, whereupon the PUID 255 send the request to the server 260 that sends a "lib open" to the processor 120, in turn sends a command to the processor 219 to open the lib 112, and the processor 219 actuates the lib-securing actuator 217, thereby releasing the lib 112 in step 417. After the user verifies in step 420 that the secure receptacle 200 contains the proper quantity of the proper medication, and optionally other information, the user inputs an approval on the PUID 255 in step 425, whereupon the PUID 255 sends the approval to the server 260 which annotates the fill record to indicate that the fill was checked and approved. If the lib 112 was opened, the process branches at decision point 430 and the user closes the lib 112 in step 432, thereby completing the check process 400.

FIG. 10 is a flow chart of an exemplary transport process 500 according to certain aspects of the present disclosure. For this example, it is presumed that the transport process 500 follows the check process 400 and that the secure receptacle 200 is still attached to the smart carrier 100. The process starts at step 505 when a user, for example a pharmacy technician, picks up a smart carrier 100 with a secure receptacle 200 docked in one of the docking locations 106. If the destination of the secure receptacle 200 is a dispensing system 10 within the same building, the process 500 branches to step 510 wherein the user places the smart carrier 100 on a cart 290 such as shown in FIG. 7. In certain embodiments, the destination of a filled secure receptacle 200 may be any of a refrigerated cabinet, a beside storage compartment in a patient's room, an infusion pump or other medical device, or a designated storage location, for example a locked inventory area. The user moves the cart 290 to the location of the dispensing system 10 in step 515 and scans a machine-readable dispenser identifier, for example a barcode, on the dispensing system 10 with the PUID 255. The PUID 255 sends this dispenser identifier to the server 260, determines which medications are intended to be loaded into this dispensing system 10, and then determines which secure receptacles 200 contain these medications and the reference identifiers of those receptacles 200.

For this example, a single medication is intended to be delivered to this dispensing system 10 and the server 260 sends the reference identifier to the processor 120 of the smart carrier 100 to which the determined secure receptacle 20 is docked. In step 525, the processor 120 activates the indicator 114 that is associated with the docking location 106 to which the determined secure receptacle 200 is docked. In step 530, the user removes the secure receptacle from the docking location 106 having the activated indicator 114 and, in step 535, docks the removed secure receptacle 200 with the dispensing system 10, thus terminating the transport process 500 for this secure receptacle 200. Step 535 may include additional activities to log into the dispensing system 10 and open the storage location, for example a drawer, prior to docking the secure receptacle 200. The user may then repeat steps 515-535 to deliver other secure receptacles 200 to other dispensing systems 10 in the same building.

If, in step 505, the user determines that the secure carrier 100 has secure receptacles 200 that are to be delivered to a dispensing system 10 in another building, for example a hospital "B" as shown in FIG. 6, that is part of a group of hospitals, then the process 500 branches to step 540 and the user places the smart carrier 100 in a tote or other transport container. The user places the tote in a vehicle, for example a van, in step 545 and a driver, which may be the same user or a different person, moves the vehicle to the destination building, e.g. the other hospital, in step 550. In step 555, the driver, or another user such as a pharmacy technician, transfers the smart carrier 100 from the tote to a cart 290. This branch of process 500 then follows the steps 515-535 within this second building to complete the process.

It can be seen that the disclosed embodiments of the smart carrier, in conjunction with secure receptacles and a mobile input device, allow a pharmacist to dispense and transport medication with greater ease and improved safety but allowing them to move the disclosed systems to the location of the medications, or other convenient work locations, and not be limited by a fixed location, for example a filling station located in a fixed location in a pharmacy. The linkage of the various disclosed systems also provides improved recordkeeping as the information is immediately provided to and stored by a central server.

The previous description is provided to enable any person skilled in the art to practice the various aspects described herein. While the foregoing has described what are considered to be the best mode and/or other examples, it is understood that various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." Unless specifically stated otherwise, the terms "a set" and "some" refer to one or more. Pronouns in the masculine (e.g., his) include the feminine and neuter gender (e.g., her and its) and vice versa. Headings and subheadings, if any, are used for convenience only and do not limit the invention.

To the extent that the terms "include," "have," or the like are used in the description or the claims, such terms are intended to be inclusive in a manner similar to the term "comprise" as "comprise" is interpreted when employed as a transitional word in a claim.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

A phrase such as an "aspect" does not imply that such aspect is essential to the subject technology or that such aspect applies to all configurations of the subject technology. A disclosure relating to an aspect may apply to all configurations, or one or more configurations. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. A phrase such an embodiment may refer to one or more embodiments and vice versa.

The word "exemplary" is used herein to mean "serving as an example or illustration." Any aspect or design described herein as "exemplary" is not necessarily to be construed as preferred or advantageous over other aspects or designs.

No claim element is to be construed under the provisions of 35 U.S.C. § 112, sixth paragraph, unless the element is expressly recited using the phrase "means for" or, in the case of a method claim, the element is recited using the phrase "step for."

What is claimed is:

1. A portable carrier comprising:
  a housing including a docking location, wherein the docking location includes a retention feature formed to engage with a secure receptacle, the housing configured to be removably coupled to a cart, wherein the cart is configured to couple with a plurality of portable carriers;
  an indicator associated with the docking location;
  a wireless interface module disposed within the housing;

a processor disposed within the housing and operatively coupled to the docking location and the wireless interface module;
an energy storage device disposed within the housing, the energy storage device electrically coupled with the processor, the wireless interface module, and the docking location to provide operational power; and
wherein the docking location further includes a connector electrically coupled with the energy storage device and arranged to transmit power to the secure receptacle at the docking location,
wherein the processor is configured to:
activate the indicator when the docking location receives the secure receptacle;
receive, via the wireless interface, a command to adjust the secure receptacle; and
cause the secure receptacle to perform an adjustment corresponding to the command.

2. The portable carrier of claim 1, wherein the command includes a first identifier and wherein the processor is configured to:
retrieve a second identifier from a the secure receptacle that is mated with the docking location; and
cause the secure receptacle to perform the adjustment after determining that the first identifier matches the second identifier.

3. The portable carrier of claim 1, wherein:
the secure receptacle comprises a body, a lib having a closed position that cooperates with the body to form a compartment, and a lib actuator operatively coupled to the processor, the lib actuator configured to engage the lib when not actuated so as to retain the lib in the closed position and to release the lib when actuated, thereby allowing the lib to open; and
wherein the adjustment includes actuating the lib actuator.

4. The portable carrier of claim 1, wherein:
the secure receptacle comprises a processor coupled to an interface connector; and
the processor of the portable carrier is in two-way communication with the processor of the secure receptacle through the interface connector and the connector.

5. The portable carrier of claim 1, further comprising a memory comprising instructions, wherein the processor is configured to retrieve the instructions from the memory and execute the instructions.

6. The portable carrier of claim 1, wherein the processor is further configured to transmit a command to the secure receptacle to release a securable lib that is movably coupled to a body of the secure receptacle and cooperates with the body to define a compartment within the secure receptacle when the securable lib is in a closed position, thereby allowing access to the compartment, and a dose of a medication in the compartment.

7. The portable carrier of claim 1, wherein the processor is configured to cause the receptacle to perform the adjustment by at least:
transmitting the command to a docking connector that is coupled with the processor and therethrough to a mated interface connector of the secure receptacle to retain a lib of the secure receptacle in a closed position when not actuated and to release the lib when actuated, thereby allowing the lib to open.

8. The portable carrier of claim 1, wherein the wireless interface module is communicatively coupled to a server and wherein the processor is configured to:
monitor a state of the energy storage device; and
transmit, via the wireless interface module to the server, a message reporting the state.

9. The portable carrier of claim 8, wherein the wireless interface module is configured to:
provide an identifier for the secure receptacle to the server;
retrieve a reference identifier from a database; and
access a record in the database and associate a medication with the reference identifier.

10. The portable carrier of claim 1, wherein the processor is further configured to:
close a lib to secure a dose of a medication in the secure receptacle; and
transmit a message to update a record in a database to indicate that a fill process for the secure receptacle is complete.

11. A system, comprising:
a secure receptacle comprising:
a body;
a lib movably coupled to the body, the lib having a closed position that cooperates with the body to form a compartment; and
a lib actuator configured to engage the lib when not actuated so as to retain the lib in the closed position and to release the lib when actuated, thereby allowing the lib to open; and
a portable carrier comprising:
a housing including a docking location, wherein the docking location includes a retention feature formed to engage with the secure receptacle, the housing configured to be removably coupled to a cart, wherein the cart is configured to couple with a plurality of portable carriers;
an indicator associated with the docking location;
a wireless interface module disposed within the housing;
a processor disposed within the housing and operatively coupled to the docking location, the lib actuator and the wireless interface module; and
wherein the docking location further includes a connector arranged to transmit power to the secure receptacle at the docking location,
wherein the processor is configured to:
activate the indicator when the docking location receives the secure receptacle;
receive, via the wireless interface, a command to adjust the secure receptacle; and
cause the secure receptacle to perform an adjustment corresponding to the command.

12. The system of claim 11, wherein the command includes a first identifier and wherein the processor is configured to:
retrieve a second identifier from the secure receptacle that is mated with the docking location; and
cause the secure receptacle to perform the adjustment after determining that the first identifier matches the second identifier.

13. The system of claim 11, wherein the adjustment includes actuating the lib actuator.

14. The system of claim 12, wherein the processor comprises a memory configured to store the first identifier.

15. The system of claim 12, further comprising a portable user interface device configured to scan machine-readable identifiers, wherein the secure receptacle comprises a machine-readable feature comprising a third identifier that is associated with the first identifier.

16. The system of claim 11, wherein the portable carrier further comprises a memory comprising instructions, wherein the processor is configured to retrieve the instructions from the memory and execute the instructions.

17. The system of claim 11, wherein:
the secure receptacle comprises a processor coupled to an interface connector; and
the processor of the portable carrier is in two-way communication with the processor of the secure receptacle through the interface connector and the connector.

18. The system of claim 11, wherein the processor is further configured to:
update a record in a database to indicate that the compartment is filled;
scan with the wireless interface module a machine-readable identifier disposed on the secure receptacle;
retrieve, from a record in the database, information related to a medication in the secure receptacle and display the information on a display;
verify that the medication in the secure receptacle matches the record in the database; and
update the record in the database to indicate that a check process is complete.

19. The system of claim 12, wherein the processor is further configured to:
scan with the wireless interface module a third identifier that is associated with a dispensing system;
retrieve, from a database, a reference identifier of the secure receptacle that contains a medication intended to be delivered to the dispensing system that is associated with the third identifier; and
activate an indicator associated with the docking location in which the secure receptacle is docked.

20. The system of claim 19, wherein the processor is further configured to:
remove the secure receptacle from the docking location associated with the indicator;
dock the secure receptacle; and
update a record that a transport process is complete.

* * * * *

UNITED STATES PATENT AND TRADEMARK OFFICE
CERTIFICATE OF CORRECTION

PATENT NO. : 10,777,311 B2  
APPLICATION NO. : 16/434631  
DATED : September 15, 2020  
INVENTOR(S) : Gary Bell et al.

It is certified that error appears in the above-identified patent and that said Letters Patent is hereby corrected as shown below:

In the Specification

Column 1, Line 54: Replace the whole word "lib" with --lid--.

Column 1, Line 63: Replace the whole word "lib" with --lid--.

Column 2, Line 43: Replace the whole word "lib" with --lid--.

Column 2, Line 44: Replace the whole word "lib" with --lid--.

Column 2, Line 46: Replace the whole word "lib-securing" with --lid-securing--.

Column 2, Line 47: Replace both whole words "lib" with --lid--.

Column 2, Line 49: Replace the whole word "lib" with --lid--.

Column 2, Line 50: Replace the whole word "lib-securing" with --lid-securing--.

Column 2, Line 52: Replace the whole word "lib-securing" with --lid-securing--.

Column 7, Line 9: Replace the whole word "lib" with --lid--.

Column 7, Line 10: Replace the whole word "lib" with --lid--.

Column 7, Line 12: Replace the whole word "lib" with --lid--.

Column 7, Line 17: Replace the whole word "lib-securing" with --lid-securing--.

Column 7, Line 18: Replace the whole word "lib" with --lid--.

Signed and Sealed this  
Twentieth Day of April, 2021

Drew Hirshfeld  
*Performing the Functions and Duties of the  
Under Secretary of Commerce for Intellectual Property and  
Director of the United States Patent and Trademark Office*

CERTIFICATE OF CORRECTION (continued)
U.S. Pat. No. 10,777,311 B2

Column 7, Line 19: Replace the whole word "lib-securing" with --lid-securing--.

Column 7, Line 21: Replace the whole word "lib" with --lid--.

Column 7, Line 23: Replace the whole word "lib-retaining" with --lid-retaining--.

Column 7, Line 25: Replace both whole words "lib" with --lid--.

Column 7, Line 26: Replace the whole word "lib" with --lid--.

Column 7, Line 31: Replace the whole word "lib" with --lid--.

Column 7, Line 31: Replace the whole word "lib-retaining" with --lid-retaining--.

Column 7, Line 33: Replace the whole word "lib" with --lid--.

Column 7, Line 35: Replace the whole word "lib" with --lid--.

Column 7, Line 36: Replace the whole word "lib" with --lid--.

Column 7, Line 37: Replace the whole word "lib-securing" with --lid-securing--.

Column 10, Line 2: Replace the whole word "lib" with --lid--.

Column 10, Line 14: Replace the whole word "lib" with --lid--.

Column 10, Line 15: Replace the whole word "lib" with --lid--.

Column 10, Line 17: Replace the whole word "lib" with --lid--.

Column 10, Line 18: Replace the whole word "lib-securing" with --lid-securing--.

Column 10, Line 19: Replace the whole word "lib" with --lid--.

Column 10, Line 27: Replace the whole word "lib" with --lid--.

Column 10, Line 29: Replace the whole word "lib" with --lid--.

Column 10, Line 44: Replace the whole word "lib" with --lid--.

Column 10, Line 47: Replace the whole word "lib" with --lid--.

Column 10, Line 48: Replace the whole word "lib" with --lid--.

Column 10, Line 49: Replace the whole word "lib" with --lid--.

CERTIFICATE OF CORRECTION (continued)
U.S. Pat. No. 10,777,311 B2

Column 10, Line 50: Replace the whole word "lib-securing" with --lid-securing--.

Column 10, Line 51: Replace the whole word "lib" with --lid--.

Column 10, Line 57: Replace the whole word "lib" with --lid--.

Column 10, Line 59: Replace the whole word "lib" with --lid--.

In the Claims

Column 13, Line 29 (Claim 3): Replace the whole word "lib" with --lid--.

Column 13, Line 31 (Claim 3): Replace the whole word "lib" with --lid--.

Column 13, Line 32 (Claim 3): Replace the whole word "lib" with --lid--.

Column 13, Line 33 (Claim 3): Replace both whole words "lib" with --lid--.

Column 13, Line 34 (Claim 3): Replace the whole word "lib" with --lid--.

Column 13, Line 35 (Claim 3): Replace the whole word "lib" with --lid--.

Column 13, Line 36 (Claim 3): Replace the whole word "lib" with --lid--.

Column 13, Line 49 (Claim 6): Replace the whole word "lib" with --lid--.

Column 13, Line 52 (Claim 6): Replace the whole word "lib" with --lid--.

Column 13, Line 61 (Claim 7): Replace the whole word "lib" with --lid--.

Column 13, Line 62 (Claim 7): Replace the whole word "lib" with --lid--.

Column 13, Line 63 (Claim 7): Replace the whole word "lib" with --lid--.

Column 14, Line 12 (Claim 10): Replace the whole word "lib" with --lid--.

Column 14, Line 21 (Claim 11): Replace both whole words "lib" with --lid--.

Column 14, Line 24 (Claim 11): Replace both whole words "lib" with --lid--.

Column 14, Line 25 (Claim 11): Replace the whole word "lib" with --lid--.

Column 14, Line 26 (Claim 11): Replace the whole word "lib" with --lid--.

Column 14, Line 27 (Claim 11): Replace the whole word "lib" with --lid--.

Column 14, Line 39 (Claim 11): Replace the whole word "lib" with --lid--.

Column 14, Line 60 (Claim 13): Replace the whole word "lib" with --lid--.